US006642129B2

(12) United States Patent
Liu et al.

(10) Patent No.: US 6,642,129 B2
(45) Date of Patent: Nov. 4, 2003

(54) PARALLEL, INDIVIDUALLY ADDRESSABLE PROBES FOR NANOLITHOGRAPHY

(75) Inventors: Chang Liu, Champaign, IL (US); Ming Zhang, Champaign, IL (US); David Andrew Bullen, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 10/008,719

(22) Filed: Dec. 7, 2001

(65) Prior Publication Data

US 2003/0022470 A1 Jan. 30, 2003

Related U.S. Application Data

(60) Provisional application No. 60/307,976, filed on Jul. 26, 2001.

(51) Int. Cl.[7] .......................... H01L 21/20; H01L 21/36

(52) U.S. Cl. ........................................ 438/496; 438/52

(58) Field of Search .............................. 438/52, 54, 66, 438/101, 202, 496

(56) References Cited

U.S. PATENT DOCUMENTS

| | | | |
|---|---|---|---|
| 5,363,697 A | | 11/1994 | Nakagawa |
| 5,372,930 A | | 12/1994 | Colton et al. |
| 5,666,190 A | | 9/1997 | Quate et al. |
| 5,696,491 A | * | 12/1997 | White et al. |
| 5,835,477 A | | 11/1998 | Binnig et al. |
| 5,866,807 A | * | 2/1999 | Elings et al. |
| 6,136,208 A | * | 10/2000 | Chou et al. |
| 6,189,374 B1 | * | 2/2001 | Addertin et al. |
| 6,218,086 B1 | | 4/2001 | Binnig et al. |
| 6,416,476 B1 | * | 7/2002 | Ogasawara et al. |
| 6,507,478 B1 | * | 1/2003 | Sameshima |

FOREIGN PATENT DOCUMENTS

WO    WO 00/41213    7/2000

OTHER PUBLICATIONS

Despont et al., Patent Application Publication No. US 2001/0038598, published on Nov. 8, 2001.

Ming Zhang, David Bullen, Kee S. Ryu, Chang Liu, (University of Illinois at Urbana–Champaign), Seunghun Hong, Sung–Wook Chung, and Chad A. Mirkin (Northwestern University), "Passive and Active Probe Arrays for Dip–Pen Nanolithography".

David Rotman, "Nanotech Goes To Work (Technology Information)", Technology Review (Cambridge, Mass.), vol. 104, No. 1, pp. 62–68, Jan. 1, 2001.

Jin Zhu, "Chemical and physical methods for the modification of high–temperature superconductors, nanoparticles and other inorganic substrates (Abstract)", The Sciences and Engineering, vol. 60–12B, pp. 6102, 1999.

Dana A. Weinberger, Seunghun Hong, Chad A. Mirkin, B.W. Wessels, Thomas B. Higgins, "Combinatorial generation and analysis of nanometer–and micrometer–scale silicon features via 'dip–pen' nanolithography and wet chemical etching", Advanced Materials, vol. 12, No. 21, pp. 1600–1603, Nov. 2000.

(List continued on next page.)

*Primary Examiner*—Phuc T. Dang
(74) *Attorney, Agent, or Firm*—Greer, Burns & Crain, Ltd.

(57) ABSTRACT

A microfabricated probe array for nanolithography and process for designing and fabricating the probe array. The probe array consists of individual probes that can be moved independently using thermal bimetallic actuation or electrostatic actuation methods. The probe array can be used to produce traces of diffusively transferred chemicals on the substrate with sub-1 micrometer resolution, and can function as an arrayed scanning probe microscope for subsequent reading and variation of transferred patterns.

31 Claims, 8 Drawing Sheets

OTHER PUBLICATIONS

Michael Gross, "Incredible nanoplotter", Chemistry in Britain, vol. 36, No. 10, p. 25, Oct. 2000.

Chad A. Mirkin, "DNA–based Methodology for Preparing Nanocluster Circuits, Arrays, and Diagnostic Materials", MRS Bulletin, vol. 25, No. 1, pp. 43–54, 2000.

Seunghun Hong, C.A. Mirkin, "A nanoplotter with both parallel and serial writing capabilities", Science, vol. 288, No. 5472, pp. 1808–1811, Jun. 9, 2000.

N.A. Amro, S. Xu, Gang–Yu Liu, "Patterning surfaces using tip–directed displacement and self–assembly", Langmuir, vol. 16, No. 7, pp. 3006–3009, Apr. 4, 2000.

S. Hong, J. Zhu, C.A. Mirkin, "Multiple ink nanolithography: toward a multiple–pen nano–plotter", Science, vol. 286, No. 5439, pp. 523–525, Oct. 15, 1999.

R.D. Piner, Jin Zhu, Feng Xu, Seunghun Hong, C.A. Mirkin, ""Dip–Pen" nanolithography", Science, vol. 283, No. 5402, pp. 661–663, Jan. 29, 1999.

* cited by examiner

PARALLEL, INDIVIDUALLY ADDRESSABLE PROBES FOR NANOLITHOGRAPHY

RELATED APPLICATIONS AND PRIORITY CLAIM

This application claims priority of U.S. Provisional Patent Application No. 60/307,976, filed Jul. 26, 2001, under 35 U.S.C. §119.

STATEMENT OF GOVERNMENT INTEREST

This invention was made with United States Government assistance through Defense Advanced Research Projects Agency (DARPA), Contract No. NW 0650 300 F 245. The Government has certain rights in this invention.

FIELD OF THE INVENTION

The present invention relates generally to the art of efficient and high-speed generation of fine surface patterns made of chemical resists or biological substances using micromachined or microfabricated probes.

BACKGROUND OF THE INVENTION

High-throughput lithography and surface patterning with extremely fine linewidths (e.g., on the order of 10–100 nm) are very important for the future growth of the microelectronics industry and nanotechnology. Next-generation integrated circuit technology will inevitably call for efficient and low-cost generation of features with a sub-100-nm linewidth. The emerging field of nanotechnology also requires patterning and functionalization of surfaces with a spatial resolution that is comparable with the scale of the molecules and cells that need to be manipulated and modified.

The resolution of conventional projection optical lithographic systems, still the most widely used in the microelectronics industry, is limited by optical diffraction. The resolution can be improved by using beam-based direct-writing tools with high energy and short wavelengths. High-energy beam lines, including ones that rely on electron beams and X-rays, are being used. However, such direct-write lithography systems suffer from several drawbacks. First, such systems are invariably complex and expensive. Second, these lithographic tools operate with a single beam and produce patterns in a serial manner, resulting in low throughput. Third, conventional high resolution lithography systems are not capable of depositing patterns made of biological molecules or chemical compounds. Only special chemical resists may be used.

Dip-pen Nanolithography (DPN) is a new and recently introduced method of scanning probe nanolithography. A description of DPN is contained in PCT/US00/00319, the entirety of which is incorporated herein by reference. It functions by depositing nanoscale patterns on surfaces using the diffusion of a chemical species from a scanning probe tip to the surface, sometimes via a water meniscus that naturally forms between tip and sample under ambient conditions. As a DPN tip is scanned across the surface of a substrate, molecules on the surface of the tip are transported through the water meniscus that forms between the tip and the substrate surface. Once on the surface, the molecules chemically anchor themselves to the substrate, forming robust patterns. Features in the 10 nm to many micrometer range can be fabricated with commercially available silicon nitride tips. One factor that influences the linewidth of DPN writing is the linear speed of the tip. Smaller linewidths are achieved with faster tip speeds. Other factors that influence the linewidth include the sharpness of the DPN tip and the diffusion constants of the molecules used as inks.

DPN offers a number of unique benefits, including direct writing capability, high resolution (~10 nm linewidth resolution, ultimate ~5 nm spatial resolution), ultrahigh nanostructure registration capabilities, the flexibility to employ a variety of molecules for writing compounds (including biomolecules) and writing substrates (such as Au, $SiO_2$, and GaAs), the ability to integrate multiple chemical or biochemical functionalities on a single "nano-chip", a one-layer process for patterning, and the ability to automate patterning using customized software.

DPN technology can be implemented using a low-cost commercial scanning probe microscope (SPM) instrument. In a typical setup, the DPN probe chip is mounted on an SPM scanner tube in a manner similar to commercially available SPM tips. Precise horizontal and vertical movement of the probes is attained by using the internal laser signal feedback control system of the SPM machine.

SUMMARY OF THE INVENTION

The present invention provides nanolithography, such as Dip Pen Nanolithography, as well as nanoscale imaging, with individually addressable probes in dip pen arrays. A probe array having a plurality of active probes is provided, which allows greater functionality than in conventional, single-pen DPN by allowing independent actuation of individual probes through supplying current or voltage to an actuator coupled with the probe. A plurality of independently addressable probes produces a plurality of traces of same or different chemicals.

An apparatus is provided for applying at least one patterning compound to a substrate for nanolithography. The apparatus includes an array of parallel probes, each probe including a cantilever, a tip at a distal end of the cantilever for applying one of the at least one patterning compound to the substrate, and an actuator operatively coupled to the cantilever. The probes may be configured for Dip Pen Nanolithography. The actuator is designed to be responsive to an applied current or voltage to move the cantilever, and thus move the tip away from the substrate. The contact state between individual probe tips and the writing substrate can thus be independently controlled. In the case of DPN writing, the patterning process is suspended when the probe tip leaves the substrate. A number of preferred types of embodiments are disclosed. Methods are also provided for fabricating active probe arrays.

In one preferred type of embodiment of the invention, the actuator deflects the cantilever in response to applied electrical current to move the tip relative to the substrate. The actuator may be thermally operated.

According to a preferred embodiment, a thermal actuator includes a resistive heater connected to the cantilever and a wire connecting the resistive heater to a current source. When a current is applied through the resistive heater, heat is generated due to ohmic heating, thus raising the temperature of the resistor as well as the cantilever. Due to difference in the thermal expansion coefficient of the materials for the cantilever and for the metal resistor, the cantilever will be bent selectively in response to the applied current. A patch of thin metal film can be connected to the cantilever for enhancing the extent of thermal bending.

In a second type of preferred embodiment of the invention, the actuator deflects the cantilever in response to applied voltage. The actuator may be electrostatically operated. Preferred displacement is created by applying a voltage differential between two electrodes, at least one of them being not stationary.

A preferred embodiment of an electrostatic actuator includes a paddle electrode formed at an inner end of the cantilever opposite to the tip and a counter electrode. The paddle electrode faces the counter electrode with a gap having a predefined gap spacing. When a differential electrical voltage is applied across the top electrode and the counter electrode, the resultant electrostatic attraction force bends the cantilever beam and therefore moves the tip positions.

A preferred type of method of the current invention provides a method for applying at least one patterning compound to a substrate for high-speed probe-based nanolithography. The method includes the steps of: providing an array of individually addressable probes, each probe having a tip on a distal end; coating tips with same or different chemical substances; positioning the tips of the array of individually addressable probes over the substrate so that the tips are in contact with the substrate; raster-scanning the probes over the substrate surface; and selectively actuating at least one selected probe from the array of probes to move the tip of the selected probe away from the substrate. Accordingly, the selected probe does not apply patterning compound to the substrate when selected, while the non-selected probes apply at least one patterning compound to the substrate. Arbitrary two-dimensional patterns can be produced by raster-scanning the chip that contains the arrayed probes while controlling the position of individual probes during the scanning process. The probes may be configured for Dip Pen Nanolithography. The probes can also be generally applied to other nanolithography techniques where the interaction between a tip and a substrate alters the electrical, chemical, or molecular state of the surface, and may be used for imaging.

According to a preferred method of the present invention, the step of selectively actuating at least one selected probe includes the step of applying a current to a resistive heater connected to the cantilever, so that the cantilever beam is flexed. The deflection of the cantilever moves the tip away from the substrate to suspend writing on the substrate.

According to another preferred method of the present invention, the step of selectively actuating an individual probe includes applying a differential electrical voltage across a counter electrode and a moving electrode connected to an end of the selected probe. In this way, the moving and counter electrodes are moved towards one another, preferably to deflect the cantilever of the probe and move the tip away from the substrate.

DETAILED DESCRIPTION OF THE INVENTION

Generally speaking, the present invention provides active probes and active probe arrays, which are designed to achieve direct-write nanolithography, such as DPN. Devices according to the present invention can generate sub-100 nm patterns in a high speed, parallel, and controllable fashion. The active probe arrays offer greater functionality by allowing actuation of individual probes through supplying current or voltage to an actuator of the probe. The present invention is primarily directed to methods and devices for parallel DPN using active probe arrays, and methods for fabricating active probes and active probe arrays.

The active probe array can also be used for other existing or future surface patterning and lithography methods based on the scanning probe microscope (SPM) instrument family. An atomic force microscope (AFM) is considered a member of the SPM instrument family. Examples of such lithography systems include local thermal oxidation and displacement lithography.

Figure 1:
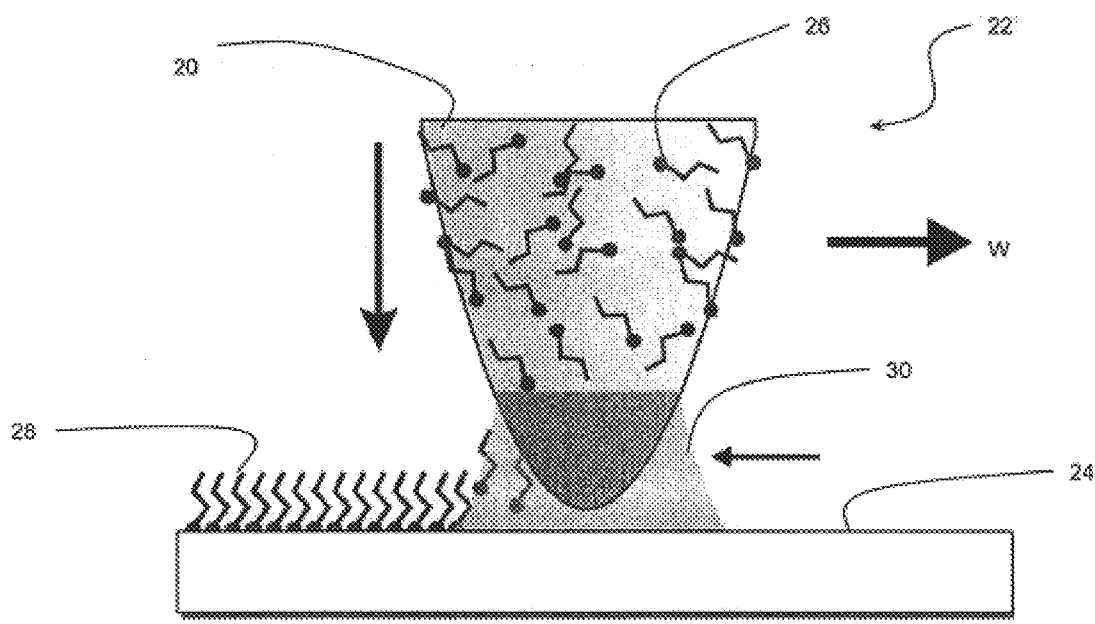
FIG. 1 is a schematic representation of the DPN process, showing a single tip coated with chemical compounds passing over a substrate (writing surface)

Referring now to FIG. 1, an example of a conventional DPN process is shown. DPN employs a tip 20 on a distal end of a cantilever of an AFM probe 22 (or other SPM probe) to deposit, or "write", nanoscale patterns onto a solid writing substrate 24, such as gold. The tip 20 applies a patterning compound 26 coated on the tip 20 to the writing substrate 24. The patterning compound 26 may be a hydrophobic patterning compound with a chemical affinity for the writing substrate 24, such as, but not limited to, 1-octadecanethiol (ODT) or mercaptohexadecanoic acid (MHA).

Similar to traditional macroscopic "dip pens" (e.g., quill, fountain, or ball-point pens, or multi-pen plotters), DPN employs molecular (capillary) transport to transfer the patterning compound 26 from the tip 20 to the writing substrate 24, forming a pattern 28 of the patterning compound. A water meniscus 30 forms between the tip 20 and the writing substrate 24 due to relative humidity in a work area, and carries the patterning compound 26 from the tip to the writing substrate as the tip is moved relatively to the writing substrate in the direction of the writing W, as indicated on FIG. 1.

Initial DPN processes involved a single probe 22 (pen). Parallel patterns also have been realized using an array of up to eight commercial probes 22 with an inter-probe spacing of 1.4 mm to write a plurality of patterns 28 on the writing substrate 24. This technique also allows application of multiple patterns 28, where each pattern contains a different patterning compound, such as a biocompound. Parallel writing is also useful, for example, to form patterns 28 during integrated circuit formation. Examples of parallel probe structures can be found in R. Piner et al., "Dip-Pen" Nanolithography, *Science,* 1999, v. 283, pp. 661–663; S. Hong et al., Multiple Ink Nanolithography: Toward a Multiple-Pen Nano-Plotter, 1999, v. 286, pp. 523–525; S. Hong et al., A Nanoplotter with Both Parallel and Serial Writing Capabilities, *Science,* v. 288, pp. 1808–1811.

Conventional parallel probe DPN processes are performed using commercially available AFM probes 22. Individual probes 22 cannot be moved independently from one another. Hence, all probes 22 must move simultaneously. Also, the inter-probe spacing of current parallel DPN arrays is too large for certain DPN applications and cannot fully satisfy the needs for a high-throughput and high-density arrayed DPN writing system. The present invention provides a nanoplotter with an array of independently active, microfabricated, closely spaced DPN probes.

Figure 2:
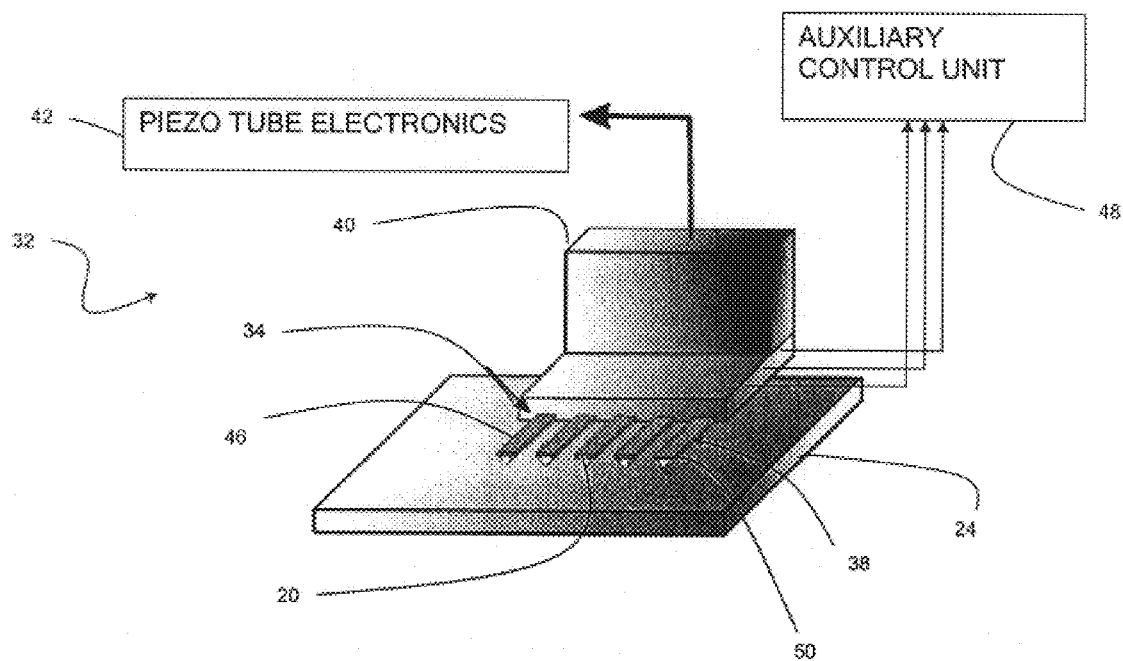
FIG. 2 is a schematic diagram of a parallel nanolithography writing system having a probe array according to one type of embodiment of the present invention, interfaced with an auxiliary control unit.

FIG. 2 shows a schematic view of an active multi-pen, parallel DPN writing system 32 according to one type of embodiment of the current invention. A DPN probe chip 34 having a probe array including a plurality of active probes 38 is mounted on an AFM scanner tube 40 in a manner similar to standard single-tip AFM probes. AFM feedback electronics 42, typically piezo tube electronics, control horizontal and vertical movement of the probe chip 34.

As the tips 20 of the active probes 38 are in contact with the writing substrate 24, an integrated actuator 46 controlled by a connected auxiliary control circuit 48 directs individual movement of the tips, preferably while the probe chip 34 is raster-scanned along the substrate 24 for patterning. The location of the integrated actuator 46 indicated in FIG. 2 is illustrative, and other actuator locations are contemplated. The term "in contact" is intended to refer to a sufficient proximity between the tips 20 and the substrate 24 to allow patterning of the patterning compound 26. When supplied with current or voltage from the control unit 48 via the probe chip 34, the actuator 46 moves a cantilever 50 of the active probe 38 to lift the tip 20 at an end of the cantilever off the writing substrate 24. This suspends the chemical deposition process. In this way, the active probe 38 can be individually controlled through selective application of current or voltage to create arbitrary patterns with high throughput.

Figure 3:
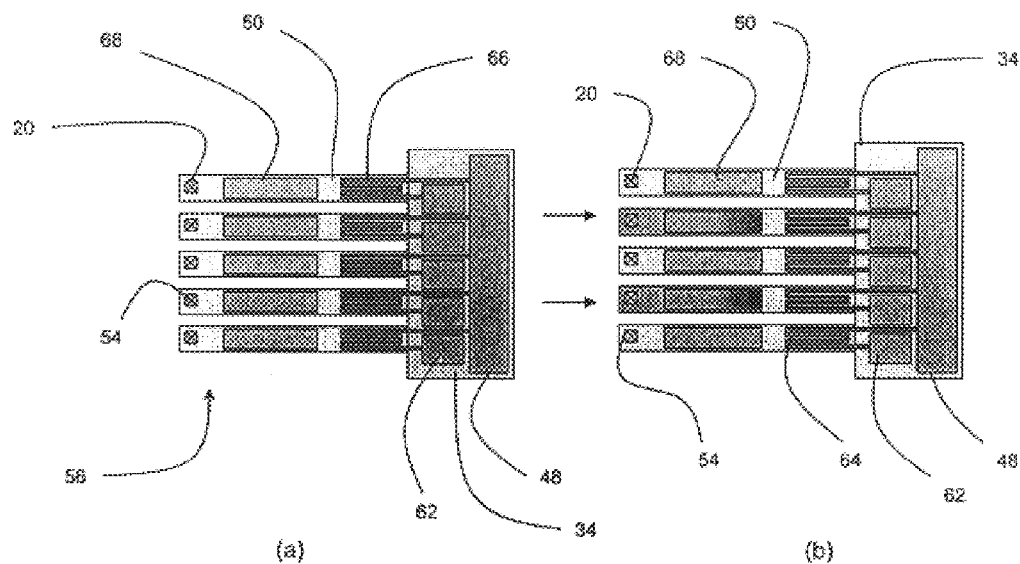
FIGS. 3a–3b are schematics of an array of bimetallic thermally actuated probes before and after deflection of selected probes, respectively, according to a preferred type of embodiment of the present invention.

FIGS. 3a and 3b show an array 56 of thermally actuated probes 54 according to a preferred type of embodiment of the present invention, before and after actuation of selected probes, respectively. In FIG. 3a, the array 56 is shown having five thermally actuated probes 54, none of which is actuated. In response to an applied current, and as shown in FIG. 3b, the second and fourth thermally actuated probes (indicated by arrows) are flexed upwardly (in FIGS. 3a and 3b, into the paper), thus moving their tips 20 away from the writing substrate 24, and suspending chemical deposition. It will be appreciated by those skilled in the art that the selective distribution of current to form the patterns 28 may be controlled by programming the control circuit 48.

The material of the cantilever beam 50 in the thermally actuated probes 54 preferably is silicon nitride thin film formed by low pressure chemical vapor deposition methods (LPCVD). According to a preferred type of method of the present invention, the thermally actuated probes 54 are formed by creating silicon nitride probes that include a thermal actuator having at least a resistive heater 66.

Figure 4:
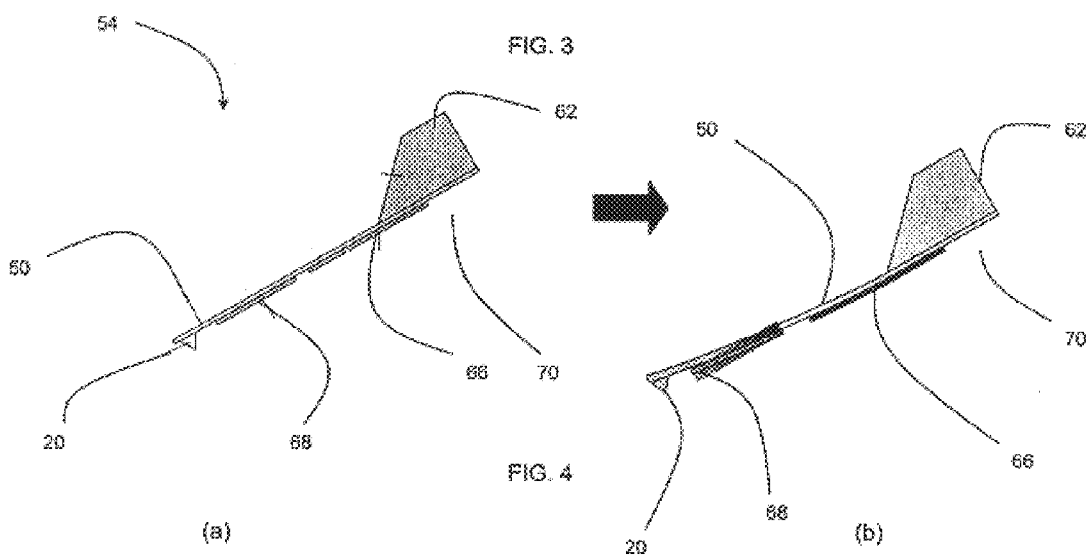
FIGS. 4a–4b are schematics of a bimetallic thermally actuated probe before and after deflection of the probe, respectively.

FIGS. 4a and 4b show one of the thermally actuated probes 54 in non-flexed and flexed (actuated) positions, respectively. The resistive heater 66, patterned onto the silicon nitride cantilever 50 of the thermally actuated probe 54, is coupled to a bonding wire 70 for carrying current to the resistive heater. The bonding wire 70 is in turn coupled to the control circuit 48 for selectively distributing current to the bonding wire 70 and thus actuating the thermally actuated probes 54. Preferably, a metal film patch 68 is connected to the cantilever 50 to increase the deflection of the probe 54.

Figure 5:
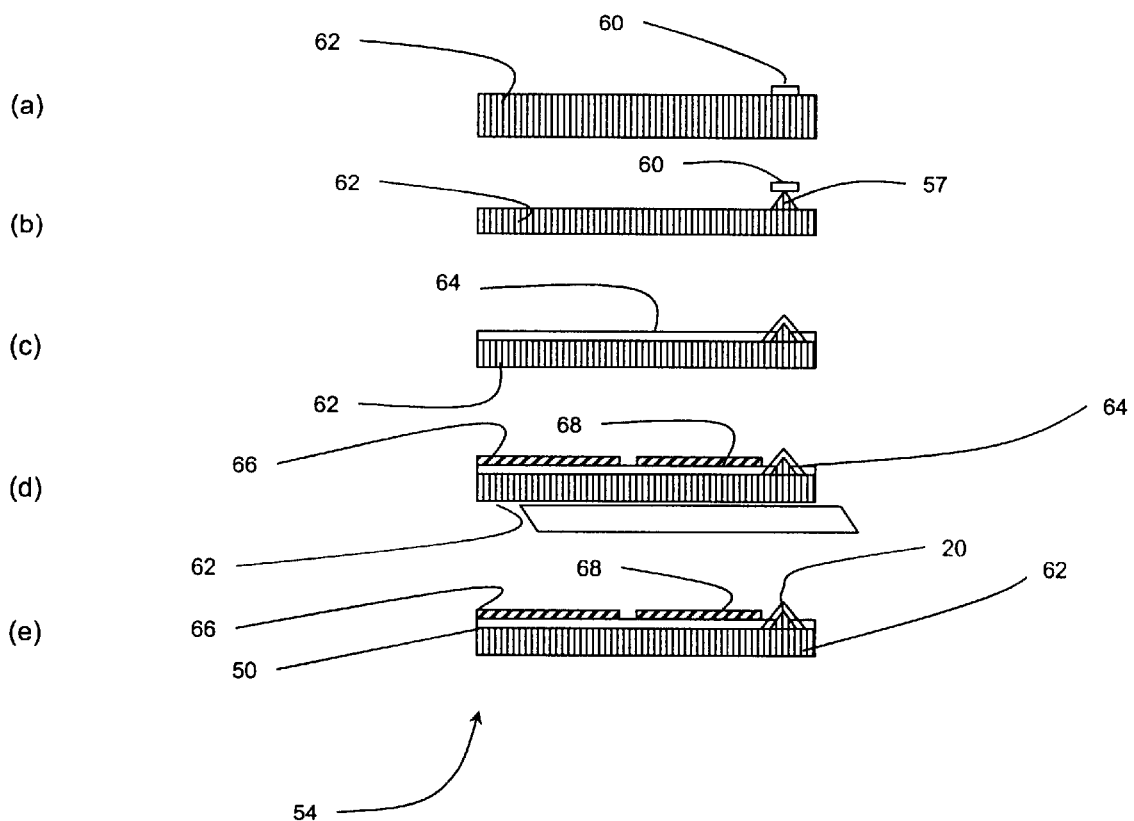
FIGS. 5a–5e are schematic drawings showing major steps in the fabrication process of a thermally actuated probe according to a preferred aspect of the invention.
Figure 6:
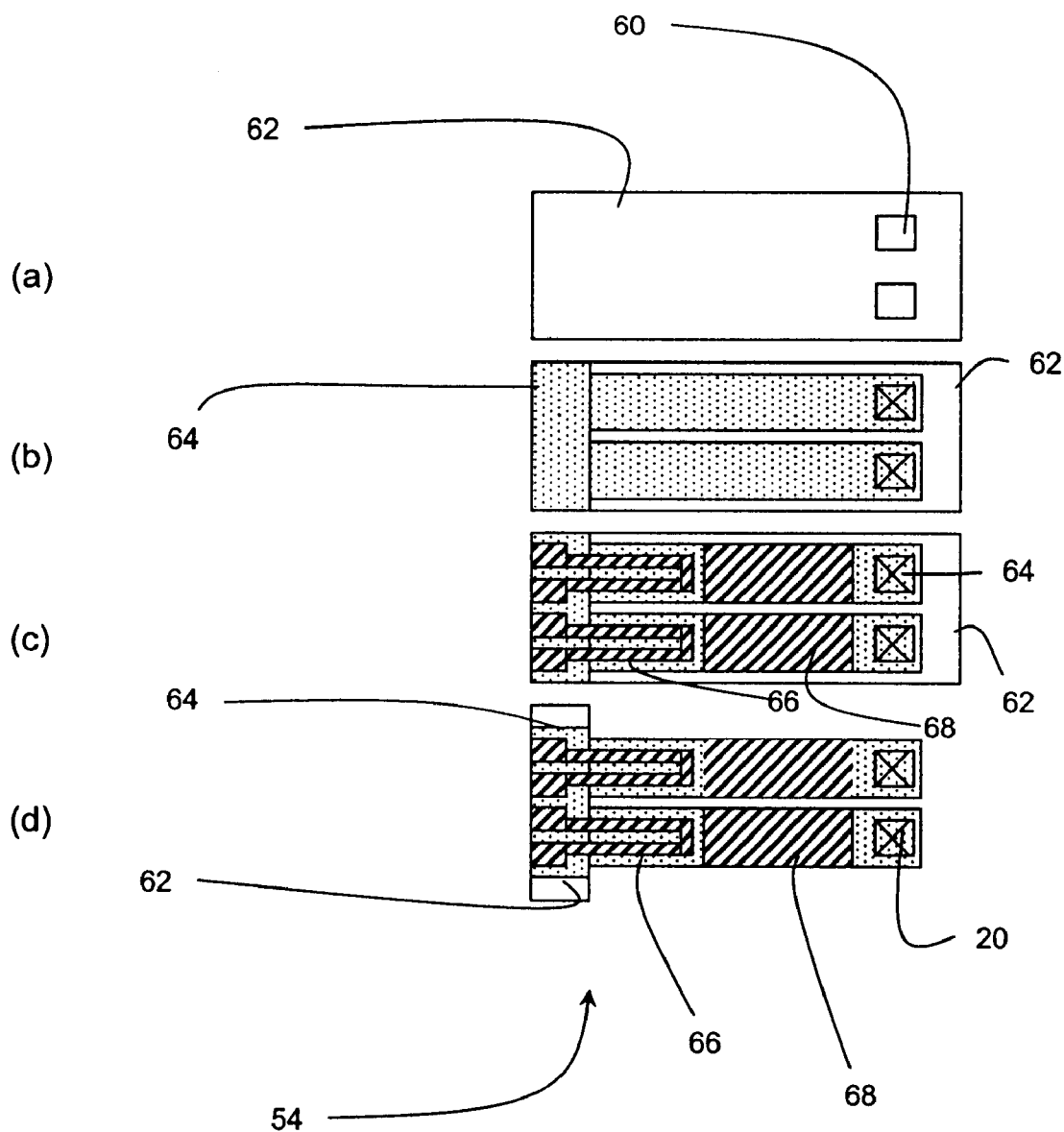
FIGS. 6a–6d are schematic drawings showing a top view of the fabrication steps shown in FIGS. 5b–5e, respectively.

FIGS. 5a–5e and 6a–6d show formation steps for the thermally actuated probe array 56, forming a single thermally actuated probe 54 and a pair of thermally actuated probes, respectively. Referring to FIG. 5a, a silicon dioxide thin film 60 is grown on a front side of a silicon substrate 62, preferably a <100>-oriented silicon wafer, to form a protective mask for creating the tip 20. The oxide layer 60 is patterned photolithographically to realize the mask for forming the tip 20. In FIG. 5b (also in FIG. 6a), a portion of the silicon substrate 62 defining the pyramidal shape of the tip 20 is formed by using anisotropic wet etching in ethylene diamine pyrocatechol (EDP). Next, as shown in FIG. 5c (6b), a layer of LPCVD silicon nitride 64 is deposited and patterned onto the etched silicon substrate 62 to define the shape of the thermally active probe 54, including the cantilever 50. As shown in FIGS. 5d (6c), the resistive (ohmic) heater 66 and the (optional) metal patch 68 are formed on the thermally active probe 54 by depositing and patterning, for example, Cr/Au onto the layer of silicon nitride 64, creating an integrated bimetallic thermal actuator. The thermally actuated probes 54 are then released by using EDP etching to undercut the support substrate 62. A portion of a silicon substrate 62 provides a handle for the thermally actuated probes 54, as shown in FIGS. 4a and 4b.

In operation, the thermally actuated probes 54, in response to an applied current, bend along their length to move the tip 20 as shown in FIG. 4b, due to differential thermal expansion of the metal for resistive heater 66 and optional patch 68 and the cantilever 50 of the thermally actuated probe. In a preferred method of operation, the control circuit 48 sends a current through the bonding wire 70 to the resistive heater 66 to bend the thermally actuated probe 54 into a circular arc of radius R due to differential thermal expansion of the silicon nitride cantilever 50 and the gold patch 68.

The expression for R under a given temperature change of $\Delta T$ is approximaely $$R = -\frac{(w_1 E_1 t_1^2)^2 + (w_2 E_2 t_2^2)^2 + 2w_1 w_2 E_1 E_2 t_1 t_2 (2t_1^2 + 3t_1 t_2 + 2t_2^2)}{6 w_1 w_2 E_1 E_2 t_1 t_2 (t_1 + t_2)(\alpha_1 - \alpha_2) \Delta T}.$$

The parameters w, t, E and $\alpha$, respectively, are the width, thickness, Young's modulus of elasticity, and the coefficient of thermal expansion of two constituent materials, denoted as materials 1 and 2. The subscripts correspond to these two materials. The temperature of a thermal actuator is dictated by the heat balance of the beam. Heat is generated by ohmic heating and lost through conduction and convection.

In the thermally actuated probe 54, the bending of the cantilever beam 50 results in a deflection of the tip 20 of $\delta$:

$$\delta = R\left(1 - \cos\left(\frac{L}{R}\right)\right)$$

Accordingly, application of current I through selected bonding wires 70 causes the cantilever 50 of the thermally actuated probes 54 connected to the bonding wires to deflect upwardly and thus move the tip 20, as shown in FIG. 4b.

The throughput of probe-based nanolithography can be made very high when a large number of active probes 38 in parallel are integrated on the probe chip 34. The thermally actuated probe array 36, manufactured according to the preferred type of embodiment of the present invention described above, results in a compact nanoplotter with high probe densities (spaced 100 µm on center) and integrated sharp tips, and may be used for nanolithography and AFM imaging.

Figure 7:
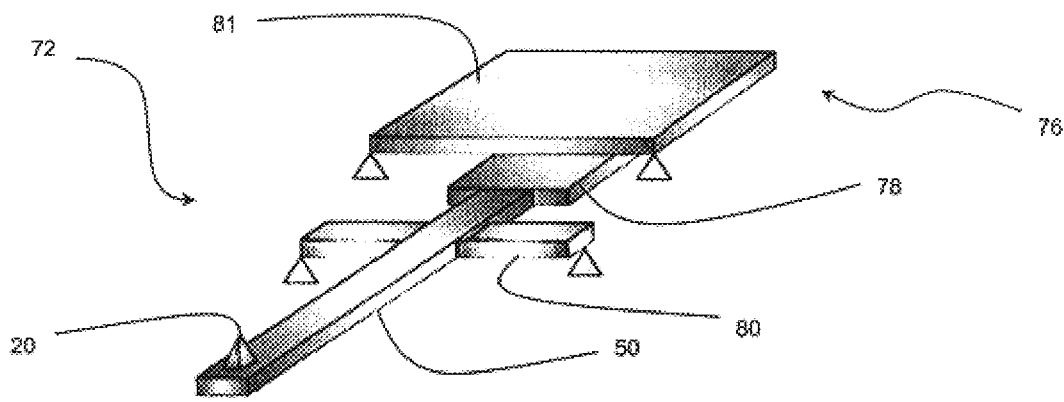
FIG. 7 is a schematic drawing of an electrostatically actuated probe according to a preferred type of embodiment of the invention.

According to another preferred type of embodiment of the present invention, an electrostatically actuated probe 72, shown in a preferred type embodiment in FIG. 7, is provided. Preferably, the probe 72 is formed as a unit of an electrostatic probe array 74, shown in a preferred embodiment in FIG. 8 in combination with the probe chip 34.

Figure 8:
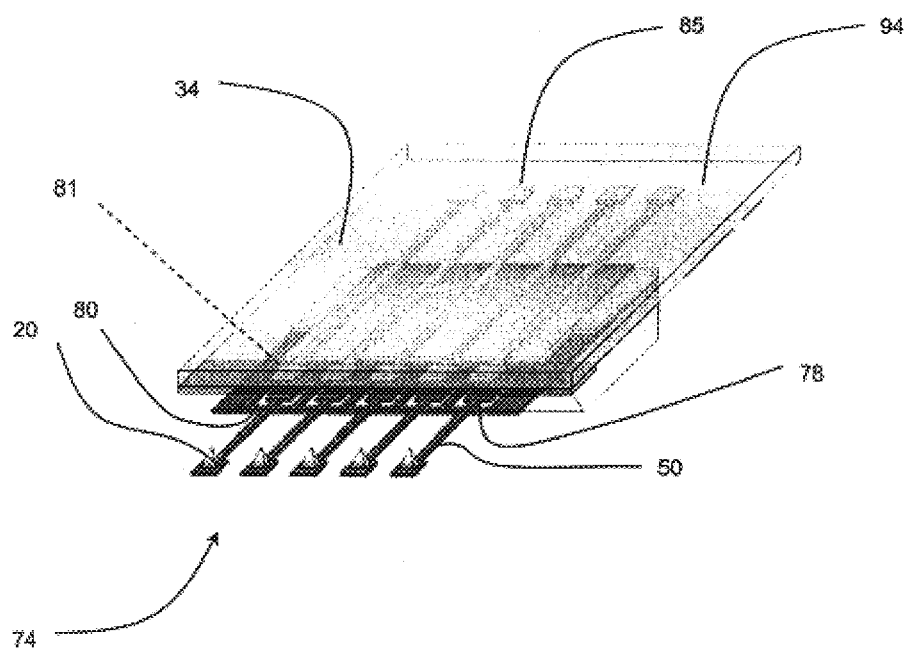
FIG. 8 is a schematic drawing of an array of electrostatically actuated probes according to a preferred type of embodiment of the invention.

As shown in FIGS. 7 and 8, the electrostatically actuated probe 72 includes an electrostatic actuator 76, which may include a paddle-shaped plate 78 at the inner longitudinal end of the cantilever 50, longitudinally opposite to the tip 20. The paddle-shaped plate 78 is preferably integrally formed with the electrostatically actuated probe 72. The electrostatic actuator 76 further includes a counter electrode 81, which is preferably stationary, and may be formed on the probe chip 34, for electrostatically interacting with the paddle-shaped plate 78. The counter electrode 81 may be formed as part of a parallel array of electrodes electrically connected to a number of bonding pads 85 longitudinally opposed to the counter electrodes, and both are patterned, adhered, or otherwise formed or attached to a glass substrate 94 which, in the completed embodiment, covers the array of counter electrodes and connecting bonding pads. The bonding pads 85 are preferably electrically connected to the control circuit 48 for selectively applying a voltage to one or more of the bonding pads. Methods for manufacturing the glass layer 94 including the counter electrodes 81 and the bonding pads 85 will be apparent to those in the art.

It is preferred that the electrostatically actuated probe 72 is also supported at or near the midpoint of the cantilever 50 by a compact, soft spring 80, for providing torsion support to the electrostatically actuated probe, allowing deflection and thus angular motion of the probes, for moving the tips 20 of the probes. As shown in FIG. 8, the spring 80 for each of the array 74 of electrostatically actuated probes 72 is preferably a section of a unitary piece (such as a twist beam) laterally extending through each individual probe. It is further preferred that each section of the spring 80 have a relatively small cross section along the longitudinal direction of the cantilever 50. As one in the art will appreciate, dimensions of the spring 80 such as the cross-sectional area can be varied depending on boundary conditions to control the angular flexibility of the cantilever 50.

Figure 9:
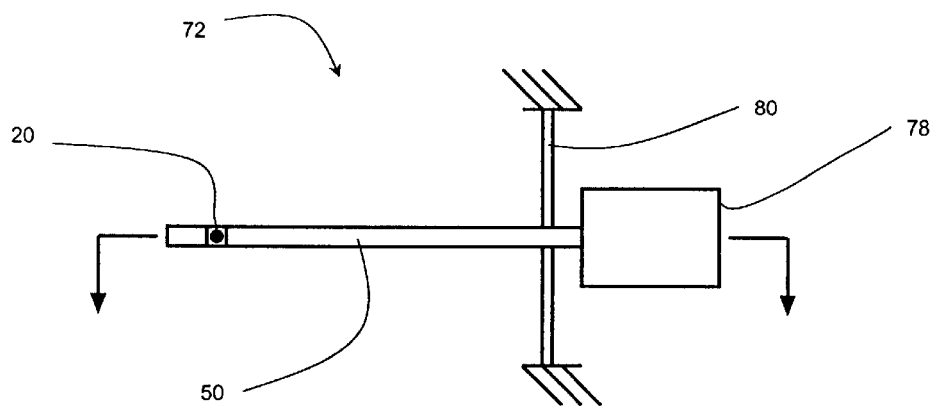
FIG. 9 is a schematic showing a top view of an electrostatic actuator probe.

FIG. 9 is a top view of a preferred embodiment of the electrostatically actuated probe 72. It is preferred, though not required, that the cantilever 50, paddle-shaped plate 78, and soft spring 80 be formed integrally from boron-doped silicon. This material is preferred both for its low etch rate in EDP solutions and for its relatively high electrical conductivity.

Figure 10:
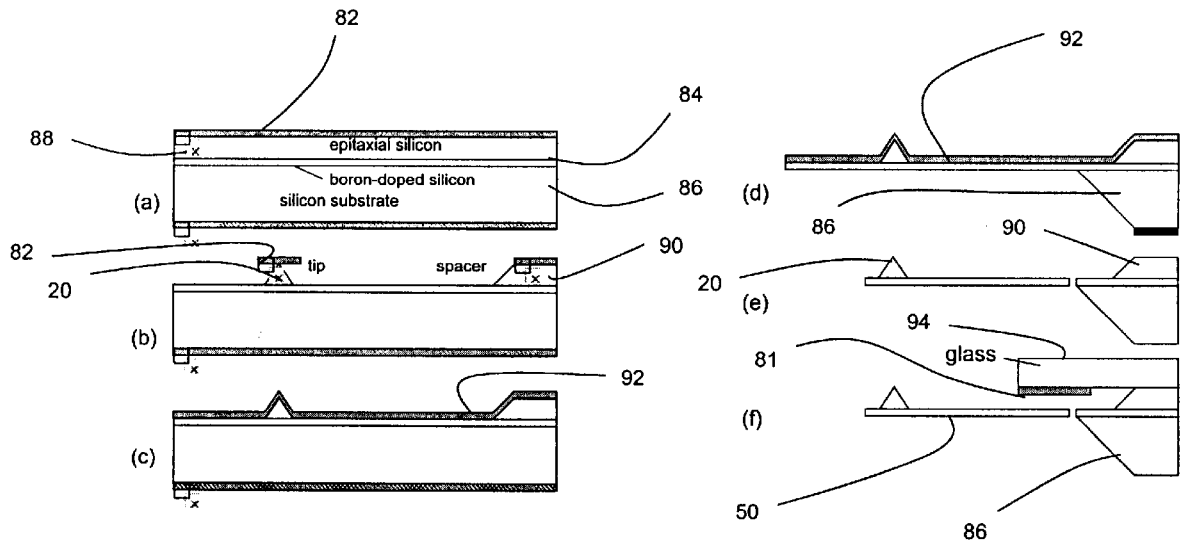
FIGS. 10a–10f are schematics taken along a section of FIG. 9 and in the direction indicated, showing fabrication steps for an electrostatically actuated probe according to a preferred method of the invention.
Figure 11:
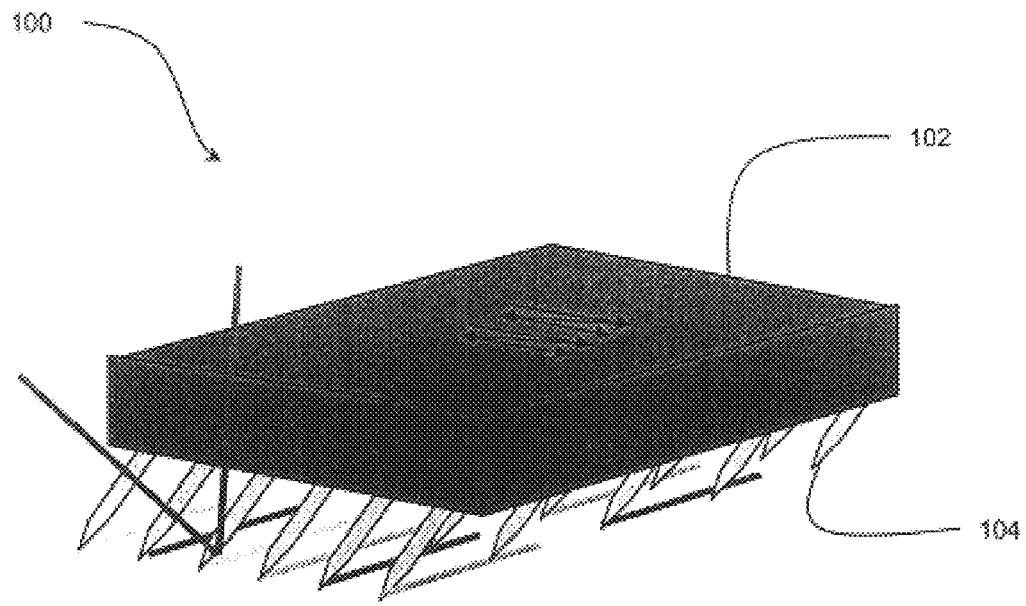
FIG. 11 is a schematic drawing of a two-dimensional array DPN nanoplotter according to another preferred embodiment of the invention.

A preferred method of fabrication of the electrostatically actuated probe 72 is shown in FIGS. 10a–10f. Referring first to FIG. 10a, a silicon dioxide layer 82 is grown on a front side of a three-layered wafer containing a heavily boron-doped silicon layer 84 sandwiched between a <100>-oriented silicon wafer 86 and an epitaxial <100>-oriented silicon layer 88. Alternatively, the silicon layer 84 may be doped by phosphorous. The silicon dioxide layer 82 defines boundaries of a mask for forming the tip 20. Furthermore, the silicon dioxide layer 82 can define boundaries for forming a spacer 90, which vertically separates the electrostatically actuated probe 72 from the counter electrode 81, which is patterned on a separate glass substrate 94. In FIG. 10b, the silicon tip 20 and the spacer 90 are formed from the epitaxial silicon wafer 88 by EDP etching. Next, as shown in FIG. 10c, a thermal oxide layer 92 is grown over the epitaxial silicon wafer 88, including the tip 20, the spacer 90, and the boron-doped silicon layer 84 to protect the front side during the final release. As shown in FIG. 10d, the silicon wafer 86 is then etched by EDP to remove material underneath the boron-doped silicon layer 84, and release the boron-doped silicon cantilever 50.

Next, as shown in FIG. 10e, the thermal oxide layer 92 is removed, and the electrostatically actuated probes 84 are formed from the boron-doped silicon layer 84, including, preferably integrally, the cantilever 50, the soft spring 80, and the paddle-shaped plate 78, for each probe in the array. As shown in FIG. 8, the portion of the cantilever 50 longitudinally disposed between the paddle-shaped plate 78 and the soft spring 80 is preferably wider in cross-sectional area along the lateral direction, i.e. in the direction of the length of the soft spring, than the distal portion of the cantilever. In this way, the deflection of the tip 20 is greater because the bending torque is fully transferred to the support spring 80. The electrostatically actuated probe 72 is released.

Finally, as shown in FIG. 10f, the layer of glass 94 and the connected counter electrode 81 are formed or placed over the spacer 90.

The preferred fabrication method results in electrostatically actuated probes 72 having a sharp tip 20 (preferably, <100 nm radius of curvature) and spaced approximately 620 µm on center. Accordingly, electrostatically actuated probes 72 according to a preferred embodiment of the present invention can be used for both DPN writing and AFM imaging.

Bonding wires 70 (not shown in FIGS. 10a–10f) preferably connect the paddle-shaped plate 78 to ground potential, while the counter electrode 81 is preferably electrically coupled to the control circuit 48 via bonding pads 85 for applying voltage to the counter electrode. It will be appreciated that the electric potentials of the paddle-shaped plate 78 and the counter electrode 81 may alternatively be reversed; i.e. the paddle-shaped plate may be coupled to a voltage source, while the counter electrode may be grounded. The modifications necessary for such an alternative embodiment will be understood by those in the art.

In a preferred method of operation, voltage is applied to the paddle-shaped plate 78 to apply potential to the paddle-shaped plate 78, while the conductive counter electrode 81 is grounded. Again, alternatively, the voltage application and grounding functions could be reversed between the top electrode 81 and the paddle-shaped plate 78. Either operation applies a differential electrical voltage across the top electrode 81 and the paddle-shaped plate 78, which are preferably separated by the spacer 90. An attractive force develops between the plates of the counter electrode 81 and the paddle-shaped plate 78 that pulls them toward each other, thus tilting the cantilever 50, and preferably angularly deflecting the cantilever 50 about the soft spring 80, to move the tip 20 away from the substrate 24. As in the thermally actuated probes 54, the tip 20 can thus be selectively lifted to suspend the writing (or imaging) process.

A number of preferred embodiments have been described for active, one-dimensional arrays. However, arrays are possible in two dimensions as well. FIG. 12 shows a two-dimensional array 100 according to another preferred embodiment of the present invention. The two-dimensional array 100 shown in FIG. 12 includes six rows and five columns of downwardly-angled probes 102. The downwardly-angled probes 102 may be produced by, for example, modifying the formation process for the thermally actuated probe array 56 to extend cantilevers of individual, thermally actuated probes 54 from cavities (replicated cells) that are preferably evenly disposed along the two-dimensional array 100. The thermally actuated probes 54 are preferably integrated into the two-dimensional array 100 due to a shorter required length for each cantilever 50. The methods for modifying steps of fabrication and operation for the thermally actuated probes 54 in the two-dimensional array 100 will be understood by those in the art.

One skilled in the art can appreciate that several inventive devices and methods for DPN arrays have been shown and described, which have various attributes and advantages. By configuring each probe to be individually addressed and actuated by application of current or voltage, either thermally or electrostatically, the active probe arrays according to embodiments of the present invention allow the formation of arbitrary patterns with added resolution, at throughput comparable to conventional methods.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. An apparatus for applying a pattern to a substrate for nanolithography, the apparatus comprising:
    at least one patterning compound;
    an array of actuated probes, said array of actuated probes being arranged in parallel, wherein each of said actuated probes comprises:
    a cantilever;
    a tip at an end of said cantilever for applying one of said at least one patterning compound to said substrate; and
    an actuator operatively coupled to said cantilever, said actuator being responsive to an applied current or voltage to move said cantilever so as to move said tip relative to said substrate.

2. The apparatus of claim 1 wherein each of said actuated probes is configured for Dip Pen Nanolithography.

3. The apparatus of claim 1 wherein
    said cantilever deflects in response to said current or voltage from a current or voltage source to move said tip.

4. The apparatus of claim 3 wherein said actuator is a thermal actuator.

5. The apparatus of claim 3 wherein said actuator is an electrostatic actuator.

6. The apparatus for applying at least one patterning compound to a subtrate for nanolithography, the apparatus comprising:
    an array of actuated probes, said array of actuated probes being arranged in parallel, wherein each of said actuated probes comprises:
    a cantilever;
    a tip at an end of said cantilever for applying one of said at least one patterning compound to said substrate; and
    an actuator operatively coupled to said cantilever, said actuator being responsive to an applied current or voltage to move said cantilever so as to move said tip relative to said substrate;
    wherein said actuator is a thermal actuator; and
    wherein said thermal actuator further comprises:
        a resistive heater connected to said cantilever, said resistive heater being selectively operable in response to said current; and
        a wire electrically connecting said resistive heater to a current source,
        whereby application of current or voltage from said current or voltage source to said resistive heater results in a deflection of said cantilever.

7. The apparatus of claim 6 wherein said thermal actuator further comprises:
    a metal patch connected to said cantilever, with said metal patch having a coefficient of thermal expansion different from the coefficient of thermal expansion of said cantilever.

8. An apparatus for applying at least one patterning compound to substrate for nanolithography, the appartus comprising;
    an array of actuated probes, said array of actuated probes being arranged in parallel, wherein each of said actuated probes comprises:
    a cantilever;
    a tip at an end of said cantilever for applying one of said at least one patterning compound to said substrate; and
    an actuator operatively coupled to said cantilever, said actuator being responsive to an applied current or voltage to move said cantilever so as to move said tip relative to said substrate;
    wherein said actuator is an electronic actuator; said electrostatic actuator further comprising:
        a first electrode formed at a second end of said cantilever opposite to said tip;
        a second electrode in electrostatic communication with said first electrode;
        at least one of said first electrode and said second electrode being coupled to said current or voltage source;
        whereby selective distribution of said voltage from said current or voltage source causes a differential electrical voltage across said first electrode and said second electrode, causing at least a portion of said cantilever to tilt.

9. The apparatus of claim 8 further comprising:
    a torsion support connected near a midpoint of said cantilever, whereby said cantilever is angularly deflected about said torsion support during operation of said electrostatic actuator.

10. The apparatus of claim 4 wherein said cantilever is comprised of silicon nitride thin film grown by a low pressure chemical vapor deposition method.

11. The apparatus of claim 5 wherein said cantilever is comprised of silicon doped by boron or phosphorous.

12. The apparatus of claim 1 wherein said array is two-dimensional.

13. A method of applying at least one patterning compound to a substrate with arbitrary patterns for nanolithography, the method comprising the steps of:
    providing a plurality of selectively actuated probes, each probe having a tip on a distal end;
    providing said tips with said at least one patterning compound;

moving said tips of said plurality of selectively actuated probes over the substrate so that said tips are near or in contact with said substrate to allow application of said at least one patterning compound;

raster-scanning said array over said substrate; and, during said raster-scanning step, selectively actuating at least one selected probe from said array of selectively actuated probes so as to move said tip of said selected probe away from said substrate, whereby said at least one selected probe does not apply said at least one patterning compound to said substrate, and whereby non-selected probes apply said at least one patterning compound to said substrate.

14. The method according to claim 13 wherein said step of selectively actuating at least one selected probe from said array of selectively actuated probes comprises the step of:

applying a current to a resistive heater coupled to said selected probe to flex a portion of said selected probe.

15. The method according to claim 13 wherein said step of selectively actuating said selected probe comprises the step of:

applying a differential electrical voltage between a first electrode and a second electrode, said first electrode being at an end of said selected probe, whereby said first and second electrodes are moved towards one another to tilt said selected probe.

16. The apparatus of claim 3 wherein the current or voltage source is configured to allow selective actuation of least one of the array of actuated probes.

17. A probe configured for selective actuation, the probe comprising:

a cantilever;

a tip at an end of said cantilever configured for applying at least one patterning compound;

a resistive heater of conductive metal connected to said cantilever, said resistive heater being selectively operable in response to a current;

a conductive path electrically connecting said resistive heater to a current source;

whereby application of current to said resistive heater results in a deflection of said cantilever.

18. The probe of claim 17 further comprising:

a metal patch connected to said cantilever, said metal patch having a coefficient of thermal expansion different from the coefficient of thermal expansion of said cantilever.

19. The probe of claim 17 wherein said resistive heater comprises Cr/Au.

20. The probe of claim 17 wherein said cantilever comprises silicon nitride.

21. A method of forming a selectively actuated probe comprising:

formin a silicon nitride cantilever on a substrate, the cantilever having a tip;

forming a metal resistive heater on the formed cantilever;

releasing the cantilever from the substrate.

22. The method of claim 21 wherein said forming a cantilever having a tip comprises depositing silicon nitride on the substrate by plasma enhanced chemical vapor deposition.

23. The method of claim 22 wherein said forming a metal resistive heater comprises patterning a Cr/Au layer on the deposited silicon nitride.

24. The method of claim 21 further comprising:

forming a metal patch on the formed cantilever.

25. The method of claim 24 wherein said forming a metal patch comprises patterning a Cr/Au layer on the deposited silicon nitride.

26. The method of claim 22 wherein said forming a cantilever having a tip further comprises etching the substrate to define the tip.

27. The method of claim 21 wherein said releasing comprises etching the substrate.

28. The method of applying at least one patterning compound to a substrate with arbitrary patterns for nanolithography, the method comprising the steps of:

selectively placing one or more of a plurality of probes in a position that is one of in contact with the substrate and out of contact with the substrate;

wherein the plurality of probes are configured to apply the at least one patterning compound to the substrate when in contact with the substrate.

29. The method of claim 28 wherein said step of selectively placing comprises:

applying at least one of current and voltage to move a tip of a selected one or more of the probes away from the substrate.

30. The method of claim 29 wherein said step of applying comprises:

applying the at least one of current an voltage to resistive heater formed on the selected one or more of the probes to cause a differential thermal expansion.

31. The method of claim 29 wherein said step of applying comprises:

applying the at least one of current and voltage to an electrode configured and disposed for electrostatic interaction with an electrode of said selected one or more probes to move the selected one or more probes.

* * * * *

UNITED STATES PATENT AND TRADEMARK OFFICE
CERTIFICATE OF CORRECTION

PATENT NO. : 6,642,129 B2
DATED : November 4, 2003
INVENTOR(S) : Liu et al.

It is certified that error appears in the above-identified patent and that said Letters Patent is hereby corrected as shown below:

Column 6,
Line 45, delete "approximaely" and insert -- approximately -- therefore.

Column 12,
Line 3, delete "formin" and insert -- forming-- therefore.

Signed and Sealed this

Twenty-first Day of September, 2004

JON W. DUDAS
*Director of the United States Patent and Trademark Office*

UNITED STATES PATENT AND TRADEMARK OFFICE
CERTIFICATE OF CORRECTION

PATENT NO.    : 6,642,129 B2
DATED         : November 4, 2003
INVENTOR(S)   : Liu et al.

It is certified that error appears in the above-identified patent and that said Letters Patent is hereby corrected as shown below:

<u>Column 1,</u>
Line 14, please delete "NW 0650 300 F 245" ane insert -- DAAD19-00-1-0414 -- therefor.

Signed and Sealed this

Sixteenth Day of November, 2004

JON W. DUDAS
*Director of the United States Patent and Trademark Office*